United States Patent [19]

Morton et al.

[11] 4,426,373

[45] Jan. 17, 1984

[54] SMOOTH DENTAL CREAM

[75] Inventors: Anthony J. Morton, Ashton under Lyne; Kenneth Harvey, Wilmslow, both of England

[73] Assignee: Colgate-Palmolive Co., New York, N.Y.

[21] Appl. No.: 417,941

[22] Filed: Sep. 14, 1982

[51] Int. Cl.³ .................... A61K 7/16; A61K 7/18
[52] U.S. Cl. ........................... 424/52; 424/49; 424/52
[58] Field of Search ..................... 424/49–58

[56] References Cited

U.S. PATENT DOCUMENTS

| 3,337,412 | 8/1967 | Elbreder | 424/49 |
| 3,903,252 | 9/1975 | Stearns et al. | 424/7.1 |
| 3,946,108 | 3/1976 | Tomlinson et al. | 424/49 |
| 4,020,154 | 4/1977 | Perla et al. | 424/49 |
| 4,022,881 | 5/1977 | Hawking | 424/49 |
| 4,251,507 | 2/1981 | Olson | 424/49 |
| 4,344,931 | 8/1982 | Aguilar | 424/52 |

Primary Examiner—Shep K. Rose
Attorney, Agent, or Firm—Robert L. Stone; Murray M. Grill; Herbert S. Sylvester

[57] ABSTRACT

A dental cream of desirable rheological properties containing a gelling agent system comprising hydroxyethyl cellulose and sodium carboxymethyl cellulose in a weight ratio of about 3:2 to 2:3.

11 Claims, No Drawings

SMOOTH DENTAL CREAM

Sodium carboxymethyl cellulose has commonly been used as the gelling agent of commercial choice in dental creams in view of its availability and the generally satisfactory rheological properties it gives to dental creams, particularly when they are made and used in temperature climates.

However, there is an observable tendency of dental creams formulated with many grades of sodium carboxymethyl cellulose to become rough (soft lump or chunk formation) in appearance even at room temperature, particularly when subjected to dynamic ageing, this is extrusion of 2 cm of dental cream ribbon from a tube twice a day for 2 weeks, a condition which simulates normal use of a dental cream by a single person.

Even grades of sodium carboxymethyl cellulose which do not undergo such roughening upon dynamic aging can reveal other rheological problems, for instance poor "stand up" qualities, that is, the rapid setting of the extruded cream into a flat ribbon.

It is noteworthy that roughening on dynamic aging is particularly observable when the dental cream contains a compound which provides fluorine and a calcium phosphate is present as polishing material. Thus, there is little problem when fluorine is provided from sodium monofluorophosphate or mixture of sodium monofluorophosphate and sodium fluoride and the polishing agent is a siliceous material. However, the problem is readily observable when fluorine is provided from sodium monofluorophosphate or a mixture of sodium monofluorophosphate and sodium fluoride in a dental cream containing at least about 35% by weight of a calcium phosphate polishing material such as dicalcium phosphate.

Attempts to overcome the roughening problem without having other problems such as poor "stand up" occur by mixing different grades of sodium carboxymethyl cellulose or mixing sodium carboxymethyl cellulose with other gelling agents such as synthetic inorganic silicated clay (e.g. materials available under the trademarks "Laponite" and "Veegum"), thickeners such as silica thickeners available from Huber under the trademark "Zeosyl" as Zeosyl 200 and from Rhone Poulenc as Tixosil 33J or available from Wacker under the identification "HDK N20", and liquid phase material such as polyethylene glycol 600 have not been satisfactory. However, in accordance with the present invention a gelling agent mixture is provided which has little susceptibility to roughness upon aging together with other desirable rheological properties such as good "stand up", absence of formation of a "tail" on an extruded ribbon of dental cream and good ribbon gloss. Moreover, dental cream can be readily manufactured with this mixture without substantial modification of procedures used when sodium carboxymethyl cellulose is the only gelling agent. The gelling material with which sodium carboxymethyl cellulose is desirably mixed in particular weight ratio is hydroxyethyl cellulose. This material too, although generally good, has not been entirely satisfactory from rheological considerations when used alone or in mixture with thickening or gelling materials other than sodium carboxymethyl cellulose. Indeed, dental creams containing grades of hydroxyethyl cellulose such as Natrosol 250 M, dicalcium phosphate and a compound which provides fluorine exhibit "tailing" and/or low "stand-up" when grades such as Natrosol 250 M are the sole gelling agent or are present with sodium carboxymethyl cellulose in a weight ratio of sodium carboxymethyl cellulose to hydroxyethyl cellulose (Natrosol 250 M and the like) of below about 2:3, e.g. about 1:10 and 3:7.

In prior art U.S. Pat. No. 4,022,881 a dentrifrice was described containing as the thickening agent 5-30% of high viscosity hydroxyethyl cellulose (e.g. Natrosol 250 H) and 70-95% sodium carboxymethyl cellulose to stabilise the sodium carboxymethyl cellulose against degradation. However, such relative amounts (e.g. 10:1 and 7:3) are not satisfactory in that they do not avoid the surface roughness which is overcome in the present invention.

It is an advantage of this invention that a gelling agent system is provided for a dental cream which remains smooth upon dynamic ageing and has other generally desirable rheological properties.

It is a particular advantage of the invention that dental cream tailing is avoided and stand up is improved even when hydroxyethyl cellulose predominates in the gelling agent system.

It is a further advantage of this invention that a dental cream comprising a compound which provides fluorine and a polishing agent including a calcium phosphate is provided which contains a gelling agent system which permits the dental cream to have generally desirable rheological properties including smoothness upon dynamic ageing, absence of tailing and good stand up.

Other advantages will be apparent from consideration of the following specification.

In accordance with certain of its aspects, this invention relates to a dental cream comprising a dental vehicle comprising about 20-80% by weight based on the weight of the dental cream of a liquid phase containing water, humectant or mixture thereof and about 0.5-5% by weight based on the weight of the dental cream of a gelling agent containing sodium carboxymethyl cellulose and hydroxyethyl cellulose, each being present in a weight ratio of about 3:2 to 2:3 with regard to the other. The foregoing numerical references to viscosity in the present specification refer to viscosities measured in a Brookfield Viscometer in 2% by weight aqueous solution at 25° C.

In accordance with certain of its further aspects, this invention relates to a dental cream as described in the foregoing paragraph, wherein the dental cream comprises a compound which provides at least about 100 ppm of fluorine and about 40-75% by weight of a dentally acceptable non-toxic water-insoluble polishing agent containing a calcium phosphate in amount of at least about 35% by weight of the dental cream.

The gelling agent is present in the dental cream in amount of about 0.5-5% by weight, preferably about 0.8-2%, and most preferably about 0.9-1.1%, the ratio of sodium carboxymethyl cellulose to hydroxyethyl cellulose being about 3:2 to 2:3, typically 1:1 and preferably less than 1:1 to 2:3 (e.g. 49:51, 9:11 or 2:3).

Sodium carboxymethyl cellulose is commercially available from Hercules as CMC-7MXF and 7MFD which are preferred grades in the practice of this invention. Grades may have a degree of polymerization in the neighborhood of 500, corresponding to a molecular weight in the neighborhood of 100,000. The viscosity is medium to high, e.g. about 300 to 3000 cps or more, typically about 300-1200 cps preferably about 300-500 cps (Brookfield, 2%, 25° C.). CMC-7MXF contains about 0.7 sodium carboxymethyl groups per anhydroglucose unit.

The following table illustrates desirable commercially available grades of sodium carboxymethyl cellulose (CMC) (where the viscosity is measured on other than a Brookfield Viscometer in 2% by weight aqueous solution at 25° C., the differences are indicated):

TABLE 1

| SUPPLIER | CMC GRADE | VISCOSITY |
| --- | --- | --- |
| Hercules | 7MXF | 300–500 |
| Hercules | 7MFD | 300–500 |
| Hercules | 9M31F | 900–1200 |
| Hercules | 9M31XF | 900–1200 |
| Hercules | 12M31XF | 900–1200 |
| Hercules | 7MF | 300–500 |
| Hercules | 12M31PD | 900–1200 |
| Hercules | 7M8SXF | 200–800 |
| Wolff Walsrode | Walocel CRT 1000 PA 07 | 700–1200 |
| Nyma | Nymcel ZMF.33* | 50–80 |
| Enka | Akucell AC 1642* | 80–120 |
| Enka | Akucell AC 1632* | 60–120 |
| Cros | Cellogen HP-SA | 700–900 |
| Uddeholm | Cekol MVEP | 500–800 |
| Hoechst | Tylose CB 200** | 120–260 |

*1% solution (Brookfield; 25° C.)
**Hoeppler Viscometer (2%; 20° C.)

Hydroxyethyl cellulose is commercially available from Hercules as Natrosol 250 M which is a preferred grade in the practice of this invention.

Grades may have a degree of polymerization in the neighborhood of 750, corresponding to a molecular weight in the neighborhood of 190,000. The viscosity is medium to high, e.g. about 3000 to 12000 cps or more, typically about 3000–7000 cps and preferably about 4500–6500 cps. (Brookfield; 2%; 25° C.). When the viscosity is measured on other than a Brookfield Viscometer in 2% by weight aqueous solution at 25° C., the differences are indicated.

The following Table illustrates desirable commercially available grades of hydroxyethyl cellulose (HEC):

TABLE 2

| SUPPLIER | HEC GRADE | VISCOSITY |
| --- | --- | --- |
| Hercules | Natrosol 250M and MR | 4500–6500 |
| Hercules | Natrosol 250 HR* and 250H* | 1500–2500 |
| Hercules | Natrosol 250 HHR* and 250 HH | 3400–5000 |
| B.P. Chemicals | Cellobond 5000A | 4200–5600 |
| B.P. Chemicals | Cellobond 7000A | 6000–7000 |
| Hoechst | Tylose H 4000P** | 3000–5000 |
| Hoechst | Tylose H10000P** | 7000–12000 |

*1% solution (Brookfield; 25° C.)
**Hoeppler Viscometer (2%; 20° C.)

The sodium carboxymethyl cellulose and hydroxyethyl cellulose may be mechanically mixed together prior to mixing with the liquid phase of the dental cream vehicle or may be mixed separately with the liquid phase.

In the dental cream formulation the dental vehicle comprises a liquid phase proportioned with the gelling agents to form an extrudible creamy mass of desirable consistency. In general, liquids in the dental cream will comprise chiefly water, glycerine, sorbitol, polyethylene glycol 400, propylene glycol, or the like including suitable mixtures thereof. It is advantageous usually to use a mixture of both water and a humectant or binder such as glycerine or sorbitol; typically about 10–30% by weight of water and about 20–50% by weight of humectant. It is preferred to use glycerine. The total liquid content will generally be about 20–80% by weight of the formulation.

The rheological advantages of this invention are evident when the dental cream contains a compound which provides at least about 100 ppm, of fluorine, typically about 100–10000 ppm, typically about 750–2000 ppm. Compounds which provide fluorine include sodium fluoride, stannous fluoride, potassium fluoride, potassium stannous fluoride, sodium hexafluorostannate, stannous chlorofluoride and sodium monofluorophosphate. Most typically in accordance with the present invention sodium monofluorophosphate or a mixture of sodium monofluorophosphate and sodium fluoride is employed. The rheological advantages are also evident when a calcium phosphate polishing agent, particularly dicalcium phosphate is present in amount of at least about 35%, by weight of the dental cream.

The dental cream typically contains about 35–75% by weight, preferably about 40–55% of a dentally acceptable water-insoluble polishing material which consists essentially of a calcium phosphate, such as dicalcium phosphate in its dihydrated or anyhydrous forms or as mixtures thereof in any desired ratio, tricalcium phosphate and calcium pyrophosphate. Most typically dicalcium phosphate is employed, generally as the dihydrate. Dicalcium phosphate is typically the sole polishing agent, but if desired minor amounts (e.g. up to about 5% by weight of the dental cream and up to about 12% by weight of the total polishing material) of other dentally acceptable water-insoluble polishing agents which do not substantially interfere with the ability of the composition of the invention to promote oral hygiene may be present. Typical polishing agents are alumina, silica, sodium aluminosilicate etc. A minor amount of hydrated alumina (e.g. about 1%) also inhibits or even eliminates the tendency of some dental creams to separate or "bleed" in their tubes.

The dental cream typically contains sodium monofluorophosphate or a mixture of sodium monofluorophosphate and sodium fluoride in amount to provide about 100–10000 ppm of fluorine, e.g. about 750–2000 ppm, of particularly about 1400–2000 such as about 1400–1670 ppm. A binary fluoride system of sodium monofluorophosphate and sodium fluoride is desirably used in which about 30–40% of the fluorine (e.g. about 30–35%, that is, about 300–580 ppm) is provided by sodium fluoride.

The gelling agent system of the present invention is particularly desirable as the gelling component of dental creams containing the binary fluorine mixture and dicalcium phosphate polishing agent described in commonly assigned printed British Patent Specification No. 20 68 727 A (Application No. 79/43642), the disclosure of which is incorporated herein by reference. Thus, in a typical dental cream, sodium monofluorophosphate is typically used in the binary system in amount to provide about 700–1090 ppm fluorine to the dental cream in which the total amount of fluorine is about 1000–1670 ppm with about 30–35% by weight to the total fluorine being provided by sodium fluoride (about 300–580 ppm). This corresponds to about 0.5–1.2% by weight of sodium monofluorophosphate and about 0.05–0.11% by weight of sodium fluoride. Preferably, the dental cream thereof contains about 1000–1500 ppm, most preferably, about 950–1000 ppm fluorine provided by sodium monofluorophosphate and about 450–500 ppm provided by sodium fluoride.

Sodium monofluorophosphate, Na$_2$PO$_3$F, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more than 1.5%, preferably not more than 1.2% of free sodium fluoride; and a sodium monofluorophosphate content of at least 12%; preferably at least 12.1% all calculated as fluoride.

As indicated above, sodium fluoride in the binary mixture is a separate fluorine-containing component from sodium monofluorophosphate. About 300–580 ppm of fluorine is preferably provided to the dental cream by sodium fluoride.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Various other materials may be incorporated in the dental creams of this invention. Examples thereof are colouring or whitening agents, preservatives, stabilisers, tetrasodium pyrophosphate, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4 (chlorobenzyl)-$N^5$-(2,4-dichlorobenzyl) biguanide;
p-chlorophenyl biguanide;
4-chlorobenzyhydryl biguanide;
4-chlorobenzylhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis (2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable, flavour and sweetening agent may together comprise from about 0.01 to 5% or more of the composition.

The dental creams should have a pH practicable for use. A pH range of 5 to 9 is particularly desirable. The reference to the pH is meant to be the pH determination directly on the toothpages. If desired, materials such as benzoic acid or citric acid may be added to adjust the pH to, say, 5.5 to 6.5.

The dental cream is typically packaged in an extrudible tube, such as lined or unlined aluminium or lead as well as a laminate tube.

The following specific examples are further illustrative of the nature of the present invention, but it is to be understood that the invention is not limited thereto. The compositions are prepared in the usual manner and all amounts of the various ingredients are by weight unless otherwise specified.

EXAMPLE 1

The following dental creams are prepared by conventional dental cream formulation technique with the sodium carboxymethyl cellulose and hydroxyethyl cellulose components being separately added to a pre-mix of glycerine and water. They are placed in aluminium dental cream tubes and dynamically aged by extruding 2 cm. of dental cream ribbon twice a day, five days a week for two weeks.

|  | PARTS | |
| --- | --- | --- |
|  | A | B |
| Glycerine | 22.00 | 22.00 |
| Sodium carboxymethyl cellulose (Hercules 7MFD) | 0.44 | 0.45 |
| Hydroxyethyl cellulose (Hercules Natrosol 250 M) | 0.46 | 0.50 |
| Dicalcium phosphate dihydrate | 48.00 | 48.00 |
| Sodium lauryl sulphate | 1.50 | 1.50 |
| Sodium saccharin | 0.20 | 0.20 |
| Sodium monofluorophosphate | 0.76 | 0.76 |
| Sodium fluoride | 0.10 | 0.10 |
| Flavour | 0.90 | 0.90 |
| Deionized water | q.s. to 100 | q.s. to 100 |

After dynamic aging for two weeks the surfaces of the dental creams are smooth and rheologically acceptable. The creams do not tail upon extrusion from the tube and stand-up well on toothbrushes. Similar rheological effects occur at a weight ratio of the sodium carboxymethyl cellulose to the hydroxyethyl cellulose of 3:2.

When the formulas are modified so that the weight ratio of the sodium carboxymethyl cellulose is greater than 3:2 (7:3 and 10:1) surface roughness is observed upon dynamic ageing; when only the sodium carboxymethyl cellulose is present as gelling agent (0.90 parts), the surface can become chunky upon completion of two weeks of dynamic aging.

When the relative amount of sodium carboxymethyl cellulose to the hydroxyethyl cellulose is below 2:3, the dental creams do not stand up well but rapidly settle into flat ribbons. Also as extrusion is completed the ribbons form tails. Tailing is also evident when the hydroxyethyl cellulose is the only gelling agent.

EXAMPLE 2

Dental Cream A of Example 1 is modified to employ 0.36 parts of sodium carboxymethyl cellulose and 0.54 parts of hydroxyethyl cellulose. The surface is smooth the dental cream does not tail and stands up well.

EXAMPLE 3

Dental Cream A of Example 1 is modified to employ 0.45 parts of sodium carboxymethyl cellulose (Hercules 7MFD) and 0.45 parts of hydroxyethyl cellulose (Hercules 250 M). The surface is smooth, the dental cream does not tail and stands up well.

Similar desirable rheology is observed when dental cream A of Example 1 is modified to employ 0.50 parts of sodium carboxymethyl cellulose (Hercules 7MF) and 0.50 parts of hydroxyethyl cellulose (Hercules 250 MR) with 0.25 parts of tetrasodium pyrophosphate also present.

Similar effects to those described in the Examples above are attained when other grades of sodium carboxymethyl cellulose (e.g. Hercules 7MXF, Wolff Walsrode Walocel CRT 1000 PAA 107, Nyma Nymcel XMF.33 and Enka Akucel AC 1632) and hydroxyethyl cellulose (e.g. Hercules Natrosol 250 HR and Natrosol 250 HHR and Hoechst Tylose H 4000P are used).

Analogous affects to those described above occur when 1.15 parts of sodium monofluorophosphate are present and sodium fluoride is omitted.

Although the invention has been described with regard to a specific example and certain variations thereof, it will be apparent to one skilled in the art that various modifications may be made thereto which fall within its scope.

We claim:

1. A dental cream which has a smooth surface and is free from formation of a tail upon extrusion comprising a dental vehicle comprising about 20–80% by weight based on the weight of the dental cream of a liquid phase containing water, humectant or mixture thereof and about 0.5–5% by weight based on the weight of the dental cream of a gelling agent containing sodium carboxymethyl cellulose having a viscosity of at least about 300 cps and hydroxyethyl cellulose having a viscosity of at least about 3000 cps, each being present in a weight ratio of about 3:2 to 2:3 with regard to the other, said viscosity being determined on a Brookfield Viscometer in 2% by weight aqueous solution at 25° C.

2. The dental cream claimed in claim 1 wherein a compound which provides at least about 100 ppm of fluorine is present and said dental cream also contains about 40–75% by weight of a dentally acceptable water-insoluble polishing agent containing a calcium phosphate in amount of at least about 35% by weight of said dental cream.

3. The dental cream claimed in claim 2 wherein about 750–2000 ppm of ionic fluorine is provided from a fluorine source selected from the group consisting of sodium monofluorophosphate a mixture of sodium monofluorophosphate and sodium fluoride in which about 30–40% by weight of said fluorine is provided by said sodium fluoride.

4. The dental cream claimed in claim 3 wherein said mixture of sodium monofluorophosphate and sodium fluoride is present and said sodium fluoride provides about 30–35% by weight of said fluorine.

5. The dental cream claimed in claim 2 wherein said gelling agent is present in amount of about 0.8–2% by weight.

6. The dental cream claimed in claim 2 wherein dicalcium phosphate is present as polishing agent in amount of about 40–50% by weight.

7. The dental cream claimed in claim 1 wherein said sodium carboxymethyl cellulose has a viscosity of about 300–500 cps and said hydroxyethyl cellulose has a viscosity of about 4500–6500 cps, each viscosity being based on measurement on a Brookfield Viscometer at 25° C. with a 2% aqueous solution.

8. A dental cream comprising a dental vehicle comprising about 20–80% by weight based on the weight of the dental cream of a liquid phase containing water, humectant or mixture thereof and about 0.5–5% by weight based on the weight of the dental cream of a gelling agent containing sodium carboxymethyl cellulose and hydroxyethyl cellulose, in a weight ratio of 49:51 to 2:3.

9. The dental cream claimed in claim 8 wherein a compound which provides at least about 100 ppm of fluorine is present and said dental cream also contains about 40–75% by weight of a dentally acceptable water-insoluble polishing agent containing a calcium phosphate in amount of at least about 35% by weight of said dental cream.

10. The dental cream claimed in claim 8 wherein said gelling agent is present in amount of from 0.8–2% by weight.

11. The dental cream claimed in claim 8 wherein said sodium carboxymethyl cellulose has a viscosity of about 300–500 cps and said hydroxyethyl cellulose has a viscosity of about 4500–6500 cps, each viscosity being based on measurement on a Brookfield Viscometer at 25° C. with a 2% aqueous solution.

* * * * *